(12) United States Patent
Lo

(10) Patent No.: US 6,554,796 B2
(45) Date of Patent: Apr. 29, 2003

(54) SAFTY HYPODERMIC SYRINGE AND NEEDLE HOLDER FOR SAME

(76) Inventor: Cheng-Chi Lo, 2F, No. 77, Ming-Sheng Rd., Yungho City, Taipei Hsien (TW)

( * ) Notice: Subject to any disclaimer, the term of this patent is extended or adjusted under 35 U.S.C. 154(b) by 156 days.

(21) Appl. No.: 09/754,328

(22) Filed: Jan. 5, 2001

(65) Prior Publication Data

US 2001/0044599 A1 Nov. 22, 2001

(30) Foreign Application Priority Data

May 22, 2000 (TW) ........................................ 89217409 U

(51) Int. Cl.[7] .................................................. A61M 5/00
(52) U.S. Cl. ........................ 604/110; 604/195; 604/196
(58) Field of Search ................................. 604/110, 162, 604/164.08, 165.01, 165.02, 194, 192, 195, 196, 197, 198

(56) References Cited

U.S. PATENT DOCUMENTS

| | | | | |
|---|---|---|---|---|
| 5,328,484 A | * | 7/1994 | Somers et al. | 604/110 |
| 5,401,246 A | * | 3/1995 | Mazur et al. | 604/110 |
| 5,531,705 A | * | 7/1996 | Alter et al. | 604/110 |
| 5,658,257 A | * | 8/1997 | Ryles | 604/110 |

* cited by examiner

Primary Examiner—Lesley D. Morris
Assistant Examiner—John Fristoe
(74) Attorney, Agent, or Firm—Bacon & Thomas, PLLC

(57) ABSTRACT

A needle holder used in a safety hypodermic syringe, including a hollow cylindrical body having a rear coupling structure adapted to receive a front retaining tip of the plunger of the safety hypodermic syringe with which the needle holder is used, wherein the needle holder has at least one movable unit and at least one engagement unit respectively connected to the hollow cylindrical body, the at least one movable unit being alternatively shifted between an extended-output status where the at least one movable unit is respectively disengaged from the at least one engagement unit, and an inwardly squeezed status where the at least one movable unit is respectively forced by an external force into engagement with the at least one engagement unit.

10 Claims, 6 Drawing Sheets

SAFTY HYPODERMIC SYRINGE AND NEEDLE HOLDER FOR SAME

BACKGROUND OF THE INVENTION

1. Field of the Invention

The present invention relates to a safety hypodermic syringe, and more particularly to such a safety hypodermic syringe, which enables the needle assembly to be received inside the barrel after its service.

2. Description of the Prior Art:

After the service of a safety hypodermic syringe, as shown in FIG. 1, the user (nurse or doctor) immediately pushes the plunger 92 forwards into engagement with the needle holder 10, and then pulls the plunger 92 backwards to receive the needle holder 10 and the needle cannula 91 inside the barrel 95.Taiwan Patent Publication #356013 discloses a similar design. However, this design of safety syringe has drawbacks. In order to let the user pull the plunger backwards with less effort after the service of the safety hypodermic syringe, the engagement power (normally friction force) between the needle holder and the inside wall of the front end of the barrel must be limited to a low level, however this design may cause the needle holder and the needle cannula to fall from position in direction toward the plunger. On the contrary, the user must employ much backward pressure to the plunger to pull the needle holder and the needle cannula back to the inside of the barrel if the engagement power between the needle holder and the inside wall of the front end of the barrel is relatively increased. Further, the production of the aforesaid safety hypodermic syringe requires high-precision fabrication equipment.

SUMMARY OF THE INVENTION

The invention has been accomplished under the circumstances in view. It is the main object of the present invention to provide a safety hypodermic syringe and a needle holder for the safety hypodermic syringe, wherein the needle holder can be shifted between an extended-out status and an inwardly squeezed status, so that the needle holder is shifted to the extended-out status and positively secured to the inside wall of the front end of the barrel of the safety hypodermic syringe during the use of the hypodermic syringe, or shifted from the extended-out status to the inwardly squeezed status for enabling g the needle holder and the needle cannula to be smoothly pulled with the plunger into the inside of the barrel after the service of the safety hypodermic syringe. According to one aspect of the present invention, the needle holder comprises a hollow cylindrical body having a rear coupling structure adapted to receive a front retaining tip of the plunger of the safety hypodermic syringe with which the needle holder is used, wherein the needle holder has at least one movable unit and at least one engagement unit respectively connected to the hollow cylindrical body, the at least one movable unit being alternatively shifted between an extended-output status where the at least one movable unit is respectively disengaged from the at least one engagement unit, and an inwardly squeezed status where the at least one movable unit is respectively forced by an external force into engagement with the at least one engagement unit. According to another aspect of the present invention, the barrel comprises an inside stop flange and an inside engagement wall portion disposed inside the inside end thereof and adapted to hold the needle holder positively in the front end of the barrel when the needle holder is shifted to the extended-out status. When pushing the plunger forwards, the at least one movable unit of the needle holder is respectively shifted from the extended-out status to the inwardly squeezed status by the inside engagement wall portion.

DETAILED DESCRIPTION OF THE PREFERRED EMBODIMENT

Figure 1:
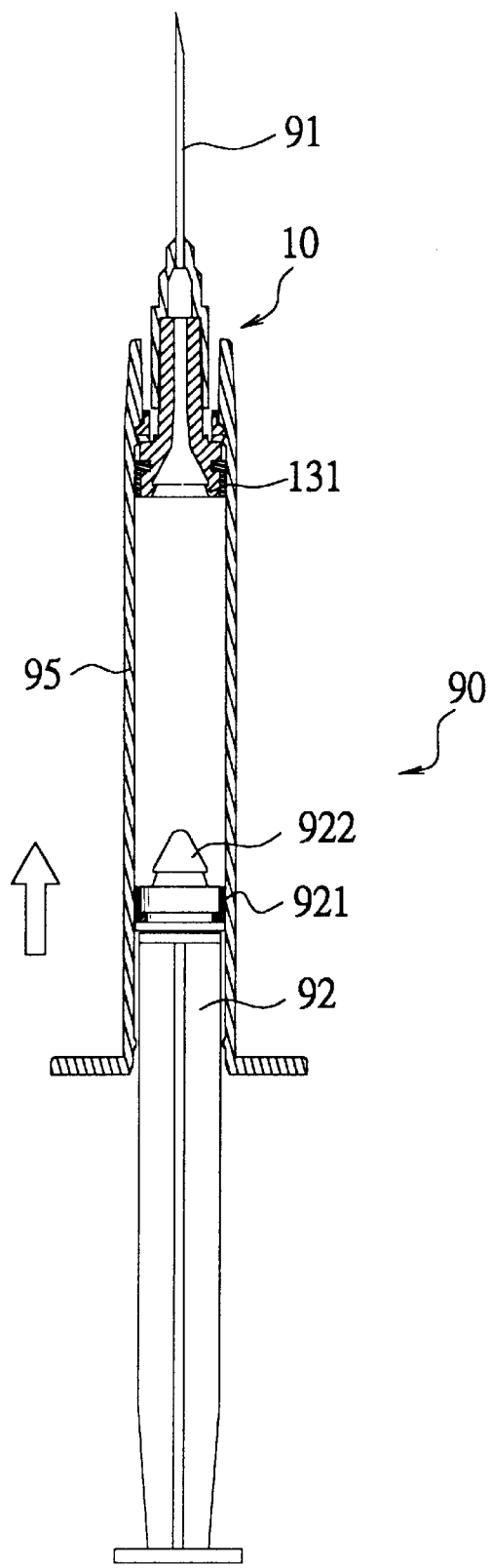
FIG. 1 is a side view in section of the present invention before the service of the safety hypodermic syringe.
Figure 2:
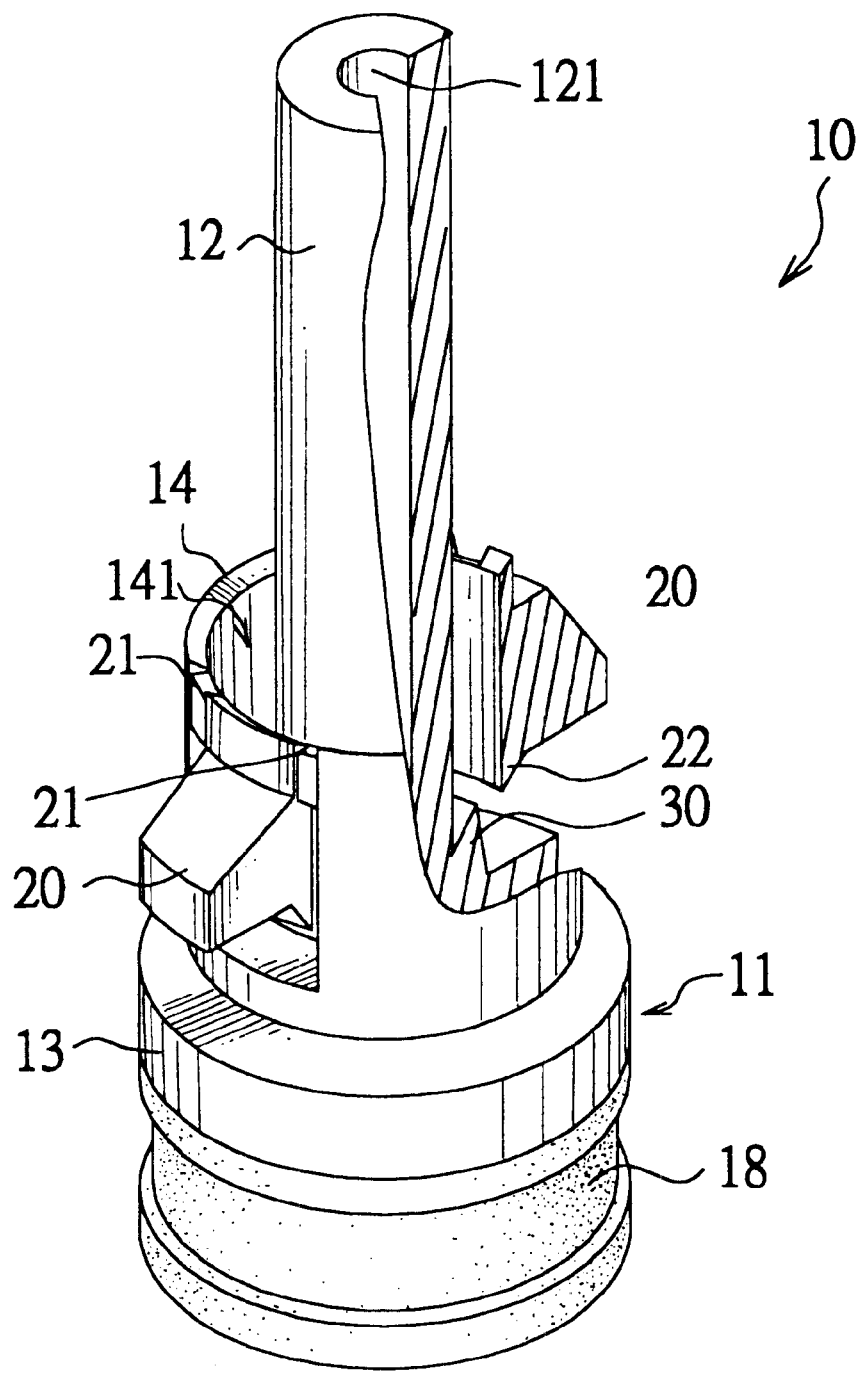
FIG. 2 is a cutaway view of a needle holder for a safety hypodermic syringe according to the present invention.
Figure 3:
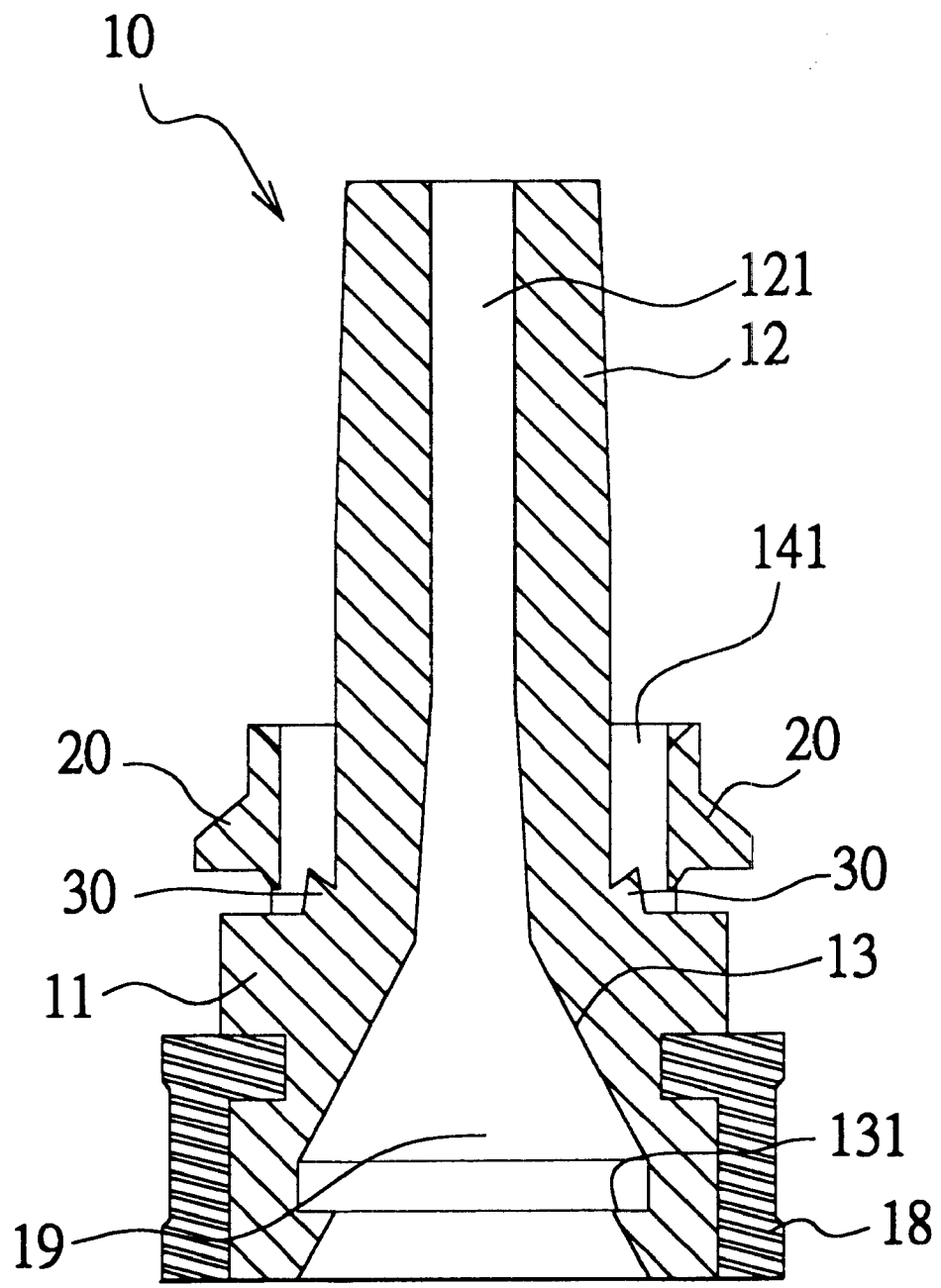
FIG. 3 is a side view in section of the needle holder shown in FIG. 2.

Referring to FIGS. from 1 through 6, a safety hypodermic syringe 90 is shown comprised of a needle cannula 91, a needle holder 10, a barrel 95, and a plunger 92 with a stopper 92. When pushing the plunger 92 forwards, the front retaining tip 922 of the plunger 92 is forced into engagement with the rear engagement portion 131 of the needle holder 10 so that the needle holder 10 and the needle cannula 91 are pulled backwards into the inside of the barrel 95 when pulling the plunger 92 backwards.

Referring to FIGS. from 2 through 6 again, the scope of the invention is the design of the movable unit 20 and engagement unit 30 of the needle holder 10. According to a first embodiment of the present invention, the needle holder 10 comprises a hollow cylindrical body 11. The hollow cylindrical body 11 comprises a front hub 12 defining a longitudinal center needle hole 121 adapted to hold the needle cannula 91, a rear coupling structure 13 defining a receiving chamber 19 adapted to receive the front retaining tip 922 of the plunger 92. The aforesaid rear engagement portion 131 is formed integral with the rear coupling structure 18 inside the receiving chamber 19, and adapted to hold the front retaining tip 922 of the plunger 92 in the receiving chamber 19. Because the rear engagement portion 131 and the front retaining tip 922 are not the main features of the design of the present invention, they are not described in detail. The engagement unit 30 is connected to the hollow cylindrical body 11 between the needle hub 12 and the rear coupling structure 13. The movable unit 20 comprises a front connecting strip 21 connected to a supporting unit 14 of the hollow cylindrical body 11, a bottom hooked portion 22, and two protruding blocks 23 sloping downwardly outwards at two opposite sides. Further, a space 141 is provided between the supporting unit 14 and the front hub 12 for enabling the lower part of the movable unit 20 to be moved inwards.

Referring to FIG. 4 again, before the use of the safety hypodermic syringe 90, the needle holder 10 is disposed in the front end 951 of the barrel 95. The barrel 95 comprises an inside stop flange 952 and an inside engagement wall portion 953. The protruding blocks 23 of the movable unit 20 are set in between the inside stop flange 952 and the inside engagement wall portion 953, keeping the needle holder 10 positively retained to the front end 951 of the barrel 95. Further, an O-ring 18 is fastened to the periphery of the rear coupling structure 13 of the hollow cylindrical body 11 to seal the gap between the needle holder 10 and the barrel 95.

Figure 4:
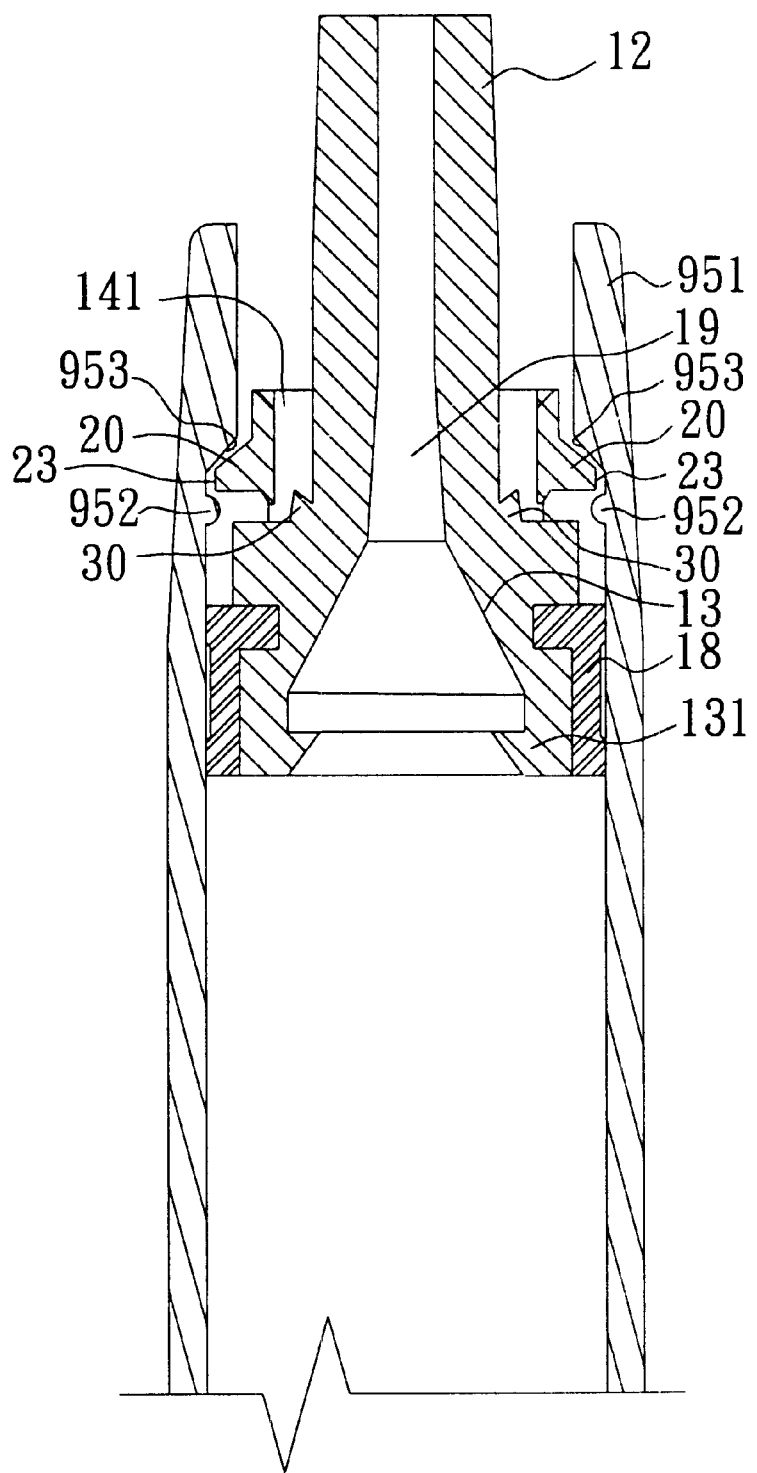
FIG. 4 is a sectional view of the present invention, showing the needle holder installed in the front end of the barrel.
Figures 5, 6:
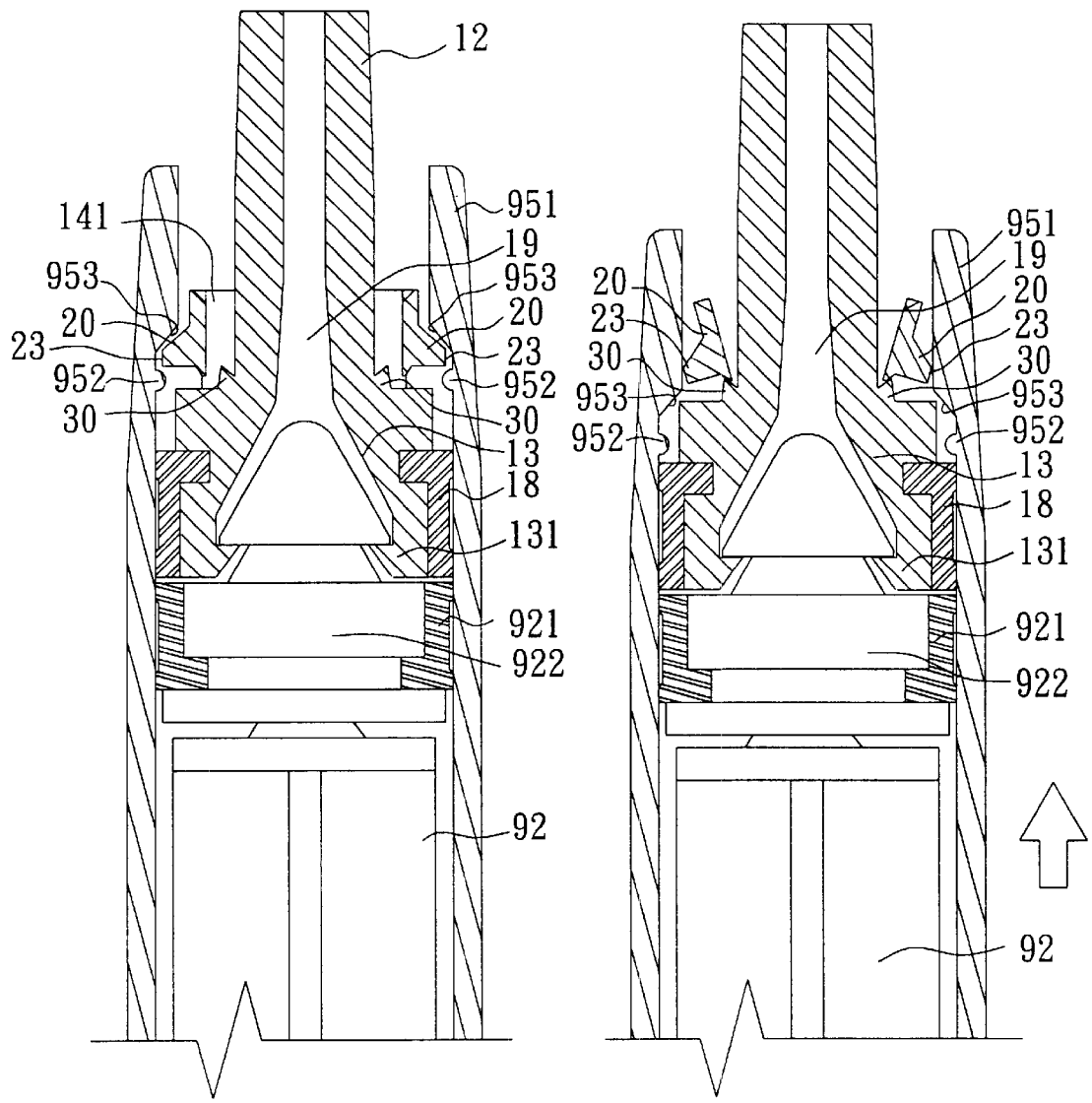
FIG. 5 is another sectional view of the present invention, showing the extended-out status of the needle holder.
FIG. 6 is still another sectional view of the present invention, showing the inwardly squeezed status of the needle holder.

FIG. 5 illustrates the plunger 92 pushed forwards, the front retaining tip 922 of the plunger 92 engaged with the rear engagement portion 131 of the rear coupling structure 13 of the needle holder 10. At this stage, medicine has been completely injected into the body of the patient. In FIGS. 4 and 5, the movable unit 20 extends out, i.e., the movable unit 20 and the engagement unit 30 are not engaged with each other. According to this embodiment, the movable unit 20 is disposed at an outer side relative to the engagement unit 30.

FIG. 6 shows the plunger 92 pushed forwards after removable of the safety hypodermic syringe 90 from the body of the patient, the movable unit 20 moved over the inside engagement portion 953 and squeezed inwards, the bottom hooked portion 22 of the movable unit 20 forced into engagement with the engagement unit 30.

According to the present invention, the needle holder 10 comprises at least one movable unit 20. Preferably, multiple movable units 20 are provided and arranged in a symmetrical relation.

Figure 7:
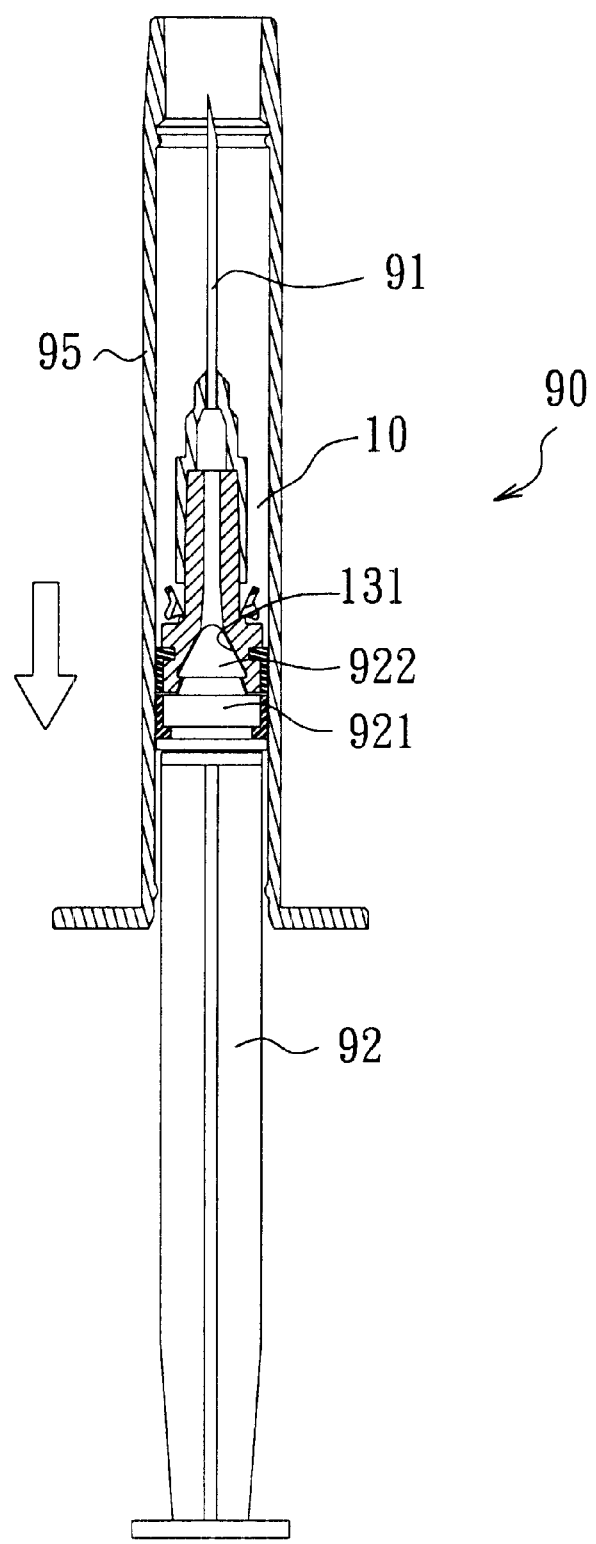
FIG. 7 is still another sectional view of the present invention, showing the plunger pulled backwards, the needle holder and the needle cannula received inside the barrel.

FIG. 7 shows the plunger 92 pulled backwards, the needle holder 10 and the needle cannula 91 received inside the barrel 95. Because the movable unit 20 is squeezed inwards, it can be moved smoothly with the plunger 92 in the barrel 95 upon backward movement of the plunger 92, and the inside stop flange 952 does not hinder backward movement of the inwardly squeezed movable unit 20.

It is to be understood that the drawings are designed for purposes of illustration only, and are not intended for use as a definition of the limits and scope of the invention disclosed.

What the invention claimed is:

1. A needle holder used in a safety hypodermic syringe, comprising a hollow cylindrical body, said hollow cylindrical body comprising a front hub adapted to hold a needle cannula, and a rear coupling structure adapted to receive a front retaining tip of the plunger of the safety hypodermic syringe with which the needle holder is used, wherein said needle holder comprises at least one movable unit and at least one engagement unit respectively connected to said hollow cylindrical body, said at least one movable unit being alternatively shifted between an extended-output status where said at least one movable unit is disengaged from said at least one engagement unit, and an inwardly squeezed status where said at least one movable unit is respectively forced by an external force into engagement with said at least one engagement unit.

2. The needle holder of claim 1 wherein said at least one movable unit is respectively disposed at an outer side relative to said at least one engagement unit when shifted to said extended-out status.

3. The needle holder of claim 1 wherein said at least one movable unit each has a front part connected to said hollow cylindrical body so that a rear part of each of said at least one movable unit is movable relative to the respective front part.

4. The needle holder of claim 3 wherein the front part of each of said at least one movable unit has a connecting strip connected to said hollow cylindrical body.

5. The needle holder of claim 3 wherein the rear part of each of said at least one movable unit comprises a bottom hooked portion adapted for engagement with said at least one engagement unit.

6. The needle holder of claim 1 wherein said at least one movable unit includes a plurality of movable units arranged in a symmetrical relationship.

7. The needle holder of claim 1 wherein the rear coupling structure of said hollow cylindrical body is peripherally mounted with an O-ring.

8. The needle holder of claim 1 wherein said at least one movable unit each comprises a protruding block.

9. A safety hypodermic syringe comprising a barrel having a front end and a rear end, a plunger moved in said barrel between the front end and rear end of said barrel, a needle holder mounted in the front end of said barrel, and a needle cannula fastened to said needle holder, said needle holder comprising a hollow cylindrical body, said hollow cylindrical body comprising a front hub, which holds said needle cannula, and a rear coupling structure adapted to receive a front end of said plunger, wherein said needle holder comprises at least one movable unit and at least one engagement unit respectively connected to said hollow cylindrical body, said at least one movable unit being alternatively shifted between an extended-output status where said at least one movable unit are disengaged from said at least one engagement unit, and an inwardly squeezed status where said at least one movable unit are respectively forced by external force into engagement with said at least one engagement unit; said barrel comprises an inside stop flange, which supports said needle holder in the front end of said barrel when said at least one movable unit is respectively shifted to said extended-out status, and an inside engagement wall portion, which secures said needle holder to said inside stop flange when said at least one movable unit is respectively shifted to said extended-out status and forces said at least one movable unit inwardly from said extended-out status to said inwardly squeezed status when said plunger is moved to the front end of said barrel.

10. The safety hypodermic syringe of claim 9 wherein said at least one movable unit each comprises a protruding block, which is stopped in between said inside stop flange and said inside engagement wall portion when at said extended-out status.

\* \* \* \* \*